US012797504B2

(12) United States Patent
Shimada et al.

(10) Patent No.: US 12,797,504 B2
(45) Date of Patent: Nov. 17, 2026

(54) DEODORIZATION TREATMENT APPARATUS AND INFORMATION COLLECTION SYSTEM

(71) Applicant: MIRAIE CORPORATION, Matsue (JP)

(72) Inventors: Yoshihisa Shimada, Matsue (JP); Shinichi Inoue, Matsue (JP); Yoshio Hirano, Matsue (JP)

(73) Assignee: MIRAIE CORPORATION, Matsue (JP)

( * ) Notice: Subject to any disclaimer, the term of this patent is extended or adjusted under 35 U.S.C. 154(b) by 637 days.

(21) Appl. No.: 18/130,380

(22) Filed: Apr. 3, 2023

(65) Prior Publication Data

US 2023/0233730 A1 Jul. 27, 2023

Related U.S. Application Data

(63) Continuation of application No. PCT/JP2021/037104, filed on Oct. 7, 2021.

(30) Foreign Application Priority Data

Oct. 8, 2020 (JP) ................................ 2020-170656

(51) Int. Cl.
*A61L 9/14* (2006.01)
*G16Y 20/00* (2020.01)

(52) U.S. Cl.
CPC .............. *A61L 9/145* (2013.01); *G16Y 20/00* (2020.01); *A61L 2209/111* (2013.01)

(58) Field of Classification Search
CPC ... A61L 9/145; A61L 2209/111; G16Y 20/00; G16Y 40/30; B01D 53/346;
(Continued)

(56) References Cited

U.S. PATENT DOCUMENTS

2018/0304195 A1 10/2018 Labaquere et al.
2022/0161189 A1 5/2022 Shimada

FOREIGN PATENT DOCUMENTS

CN 107158931 A 9/2017
JP H02119918 A 5/1990
(Continued)

OTHER PUBLICATIONS

English translation of Nakahama et al. (JP 2000140571 A) (Year: 2000).*

(Continued)

*Primary Examiner* — Maris R Kessel
*Assistant Examiner* — Aham Lee
(74) *Attorney, Agent, or Firm* — Franklin & Associates International Inc; Matthew F. Lambrinos

(57) ABSTRACT

A deodorization treatment apparatus according to an embodiment of the invention includes a deodorant tank housing microorganism-retaining carriers, supplied with odorous gas, and discharging an exhaust gas in which an odor has been removed by the microorganisms, a water sprinkler device, a water tank, a water sprinkler pipe, an exhaust pipe, a first blower, an aeration device, and a control device controlling at least one of blowing amount of the first blower, watering amount or watering frequency of the water sprinkler device, amount of air bubbles generated in liquid (Continued)

of the aeration device, water supply to the water tank, drainage from the water tank, or temperature of the deodorant tank according to measurement results.

11 Claims, 4 Drawing Sheets

(58) Field of Classification Search
CPC .......... B01D 2251/95; B01D 2257/304; B01D 2257/406; B01D 2257/90; B01D 2258/06; B01D 53/85; Y02A 50/20
See application file for complete search history.

(56) References Cited

FOREIGN PATENT DOCUMENTS

| | | | | | |
|---|---|---|---|---|---|
| JP | H0724247 | A | | 1/1995 | |
| JP | H08131760 | A | | 5/1996 | |
| JP | 2000015049 | A | | 1/2000 | |
| JP | 2000140571 | A | | 5/2000 | |
| JP | 2000176239 | A | | 6/2000 | |
| JP | 2001137651 | A | | 5/2001 | |
| JP | 2005007369 | A | | 1/2005 | |
| JP | 2005161258 | A | | 6/2005 | |
| JP | 2006116457 | A | | 5/2006 | |
| JP | 2011056339 | A | | 3/2011 | |
| JP | 2014151248 | A | | 8/2014 | |
| JP | 2015172494 | A | | 10/2015 | |
| JP | 6961138 | B1 | | 11/2021 | |
| KR | 101185027 | B1 | | 9/2012 | |
| KR | 101937705 | B1 | | 1/2019 | |
| WO | 2002035495 | A1 | | 5/2002 | |
| WO | WO-2018028243 | A1 | * | 2/2018 | B01D 53/60 |
| WO | 2020184159 | A1 | | 9/2020 | |
| WO | 2022075401 | A1 | | 4/2022 | |

OTHER PUBLICATIONS

English translation of Ono et al. (JP 2005161258 A) (Year: 2005).*
English translation of Yamamoto et al. (JP 2006116457 A) (Year: 2006).*
English translation of Harada et al. (JP 2014151248 A) (Year: 2014).*
English translation of Lee (KR 101185027 B1). (Year: 2012).*
English translation of Qiu et al. (WO 2018028243 A1) (Year: 2018).*
English translation of Written Opinion of the International Searching Authority on Dec. 7, 2021 for the PCT application No. PCT/JP2021/037104.
Partial ESR dated Oct. 11, 2024 issued in EP Appl. No. 21877700.1, in the name of Miraie Corporation.
EESR dated Jan. 14, 2025 issued in EP Appl. No. 21877700.1, in the name of Mirae Corporation.
ISR (PCT/ISA/210) dated Dec. 7, 2021, issued in PCT/JP2021/037104. English translation attached.
WO-ISA (PCT/ISA/237) dated Dec. 7, 2021, issued in PCT/JP2021/037104.
EESR dated Mar. 19, 2025 issued in EP Appl. No. 24219073.4.
Office Action dated Jun. 14, 2025 issued in CN Appl. No. 202180067961.2.
Office Action dated Dec 10, 2025 issued in CN Appl. No. 202180067961.2.
Office Action dated Oct. 21, 2025 issued in JP Appl. No. 2022-555555.
Office Action dated Mar. 13, 2026 issued in CN Appl. No. 202180067961.2.

* cited by examiner

DEODORIZATION TREATMENT APPARATUS AND INFORMATION COLLECTION SYSTEM

CROSS-REFERENCE TO RELATED APPLICATIONS

This application is a Continuation of International Patent Application No. PCT/JP2021/037104, filed on Oct. 7, 2021, which claims the benefit of priority to Japanese Patent Application No. 2020-170656, filed on Oct. 8, 2020, the entire contents of which are incorporated herein by reference.

FIELD

The present invention relates to a deodorization treatment apparatus and an information collection system. More specifically, the present invention relates to the deodorization treatment apparatus and the information collection system that control an operation according to measured values of various sensors and realize remote monitoring of an operating state.

BACKGROUND

In composting treatment facilities, drainage treatment facilities, and other facilities that emit odorous gas containing high concentrations of ammonia and exhibiting a strong offensive odor, complaints are generated from neighboring residents or the like in the case where the odorous gas is released into the atmosphere as it is. In order to achieve harmony with the local community, odor control measures have become essential.

Conventionally, as a treatment apparatus for removing offensive odors, a deodorization treatment apparatus is known in which microorganism-retaining carriers are contained in a deodorant tank, and the odor component is decomposed and deodorized by microorganisms living in the microorganism-retaining carriers.

SUMMARY

According to one embodiment of the present invention, a deodorization treatment apparatus including: a deodorant tank housing microorganism-retaining carriers retaining microorganisms, the deodorant tank supplied with odorous gas, and the deodorant tank discharging an exhaust gas in which an odor has been removed by the microorganisms, a water sprinkler device sprinkling treat water onto the microorganism-retaining carriers, a water tank connected to the deodorant tank, the water tank storing treat water flowing out from the deodorant tank, a water sprinkler pipe supplying treat water stored in the water tank to the water sprinkler device, an exhaust pipe connected to a treatment facility that emits odorous gas and supplying the odorous gas to the deodorant tank, a first blower arranged in a path of the exhaust pipe for blowing the odorous gas, an aeration device aerating the treat water stored in the water tank, and a control device measuring at least one of (1) a flow rate, an ammonia concentration, temperature or amount of dust of the odorous gas supplied to the deodorant tank, (2) an internal pressure of the deodorant tank, (3) an ammonia concentration in the exhaust gas discharged from the deodorant tank, or (4) pH, temperature, an ammonia concentration, a NO concentration, a $NO_2$ concentration, a dissolved oxygen concentration, an electric conductivity, and a water level of the treat water in the water tank, and controlling at least one of blowing amount of the first blower, watering amount or frequency of the water sprinkler device, amount of air bubbles generated in liquid of the aeration device, water supply to the water tank, drainage from the water tank, or temperature of the deodorant tank according to measurement results is provided.

According to the deodorization treatment apparatus of an embodiment of the present invention may further include a cooler arranged in the path of the exhaust pipe and cooling the odorous gas, and a gas flow resistance regulator arranged in the path of the exhaust pipe for adjusting the flow rate of the odorous gas, wherein the control device may control a cooling capacity of the cooler or an opening degree of the gas flow resistance regulator.

According to the deodorization treatment apparatus of an embodiment of the present invention may further include a second blower blowing an outside air into the path of the exhaust pipe, wherein the control device may control a blowing amount of the second blower.

According to the deodorization treatment apparatus of an embodiment of the present invention may further include a spraying device spraying a mist to the water tank, wherein the control device may control the spraying of the mist to the water tank.

According to the deodorization treatment apparatus of an embodiment of the present invention may further include a third blower blowing the outside air to the deodorant tank, wherein the control device may control a blowing amount of the third blower.

According to the deodorization treatment apparatus of an embodiment of the present invention may further include a demister arranged in the path of the exhaust pipe for filtering the odorous gas.

According to the deodorization treatment apparatus of an embodiment of the present invention, the control device may manage states of the microorganisms by controlling an volume of drainage amount discharged from the water tank.

According to the deodorization treatment apparatus of an embodiment of the present invention may further include a communication device connected to the control device and transmitting the measurement results, and a client terminal located away from the control device, the client terminal receiving the measurement results transmitted by the communication device, and the client terminal displaying the measurement results.

According to the deodorization treatment apparatus of an embodiment of the present invention, the client terminal may transmit a control signal, the communication device may receive the control signal, and the control device may control at least one of blowing amount of the first blower, watering amount or the frequency of the water sprinkler device, amount of air bubbles generated in liquid of the aeration device, water supply to the water tank, drainage from the water tank, or temperature of the deodorant tank according to the control signal received from the client terminal.

According to the deodorization treatment apparatus of an embodiment of the present invention may further include a sensor measuring the odor of the exhaust gas, wherein the control device may control blowing amount of the first blower or amount of discharge of the exhaust gas according to the measurement results.

According to one embodiment of the present invention, an information collection system including: multiple facilities that emit odorous gas, multiple deodorization treatment apparatuses connected to each of the multiple facilities emitting the odorous gas and removing the odor of the odorous gas, multiple institutions located at a location different from the multiple facilities that emit odorous gas, the multiple institutions including a sensor measuring odors of the odorous gas and at least one of wind direction, atmospheric pressure, humidity, and temperature, and a communication device transmitting measurement results of the sensor, and a client terminal located away from the sensor, the client terminal receiving the measurement results transmitted by the communication device, and the client terminal displaying the measurement results, wherein identifying an odor source from the multiple deodorization treatment apparatus by correlating the measurement results is provided.

According to the information collection system of an embodiment of the present invention, the odor source may be the deodorization treatment apparatus described above, and the control device may control blowing amount of the first blower or amount of discharge of the exhaust gas according to the measurement results.

DESCRIPTION OF EMBODIMENTS

Figure 1:
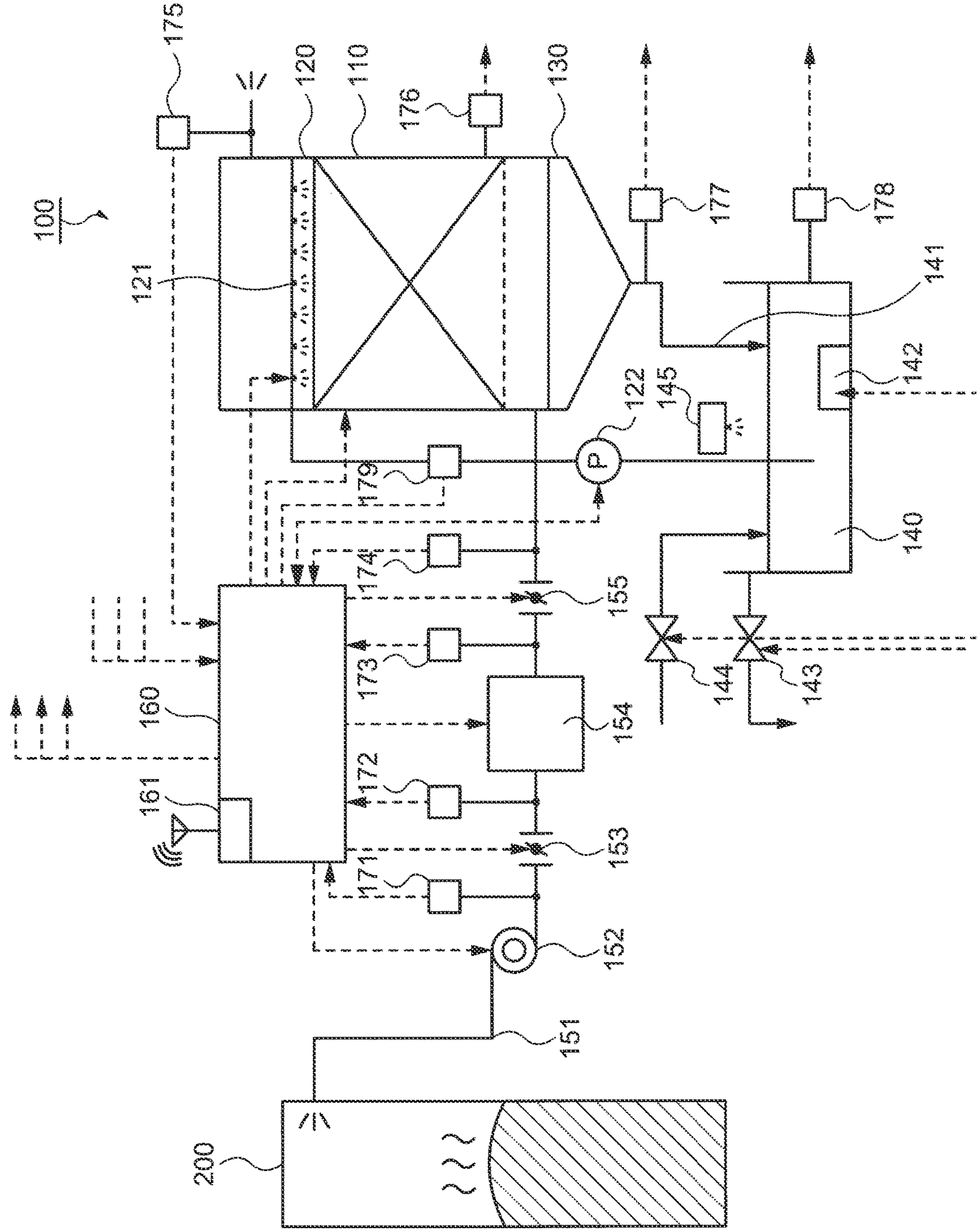
FIG. 1 is a diagram showing a configuration of a deodorization treatment apparatus according to an embodiment of the present invention.

Hereinafter, a deodorization treatment apparatus according to the present embodiment will be described in detail with reference to the drawings. In the following description, elements having substantially the same functions and configurations are denoted by the same reference signs or the same reference signs followed by alphabetic characters, and will be described redundantly only if necessary. Each of embodiments described below exemplifies an apparatus and a method for embodying the technical idea of this embodiment. The technical idea of the embodiment is not to specify the material, shape, structure, arrangement, or the like of the constituent parts as follows. Various modifications may be made to the technical idea of the embodiment with respect to the claims.

In the drawings, although widths, thicknesses, and shapes, and the like of respective portions may be schematically represented in comparison with the actual embodiments for clarity of explanation, the drawings are merely examples, and do not limit the interpretation of the present invention. In this specification and the drawings, elements having the same functions as those described with respect to the previous drawings are denoted by the same reference numerals, and redundant descriptions thereof may be omitted.

In this specification, the phrase "a includes A, B, or C," "a includes any of A, B and C," and "a includes one selected from the group consisting of A, B and C" does not exclude cases where a includes multiple combinations of A to C unless otherwise indicated. Furthermore, these expressions do not exclude the case where a includes other elements.

The following embodiments can be combined with each other as long as there is no technical inconsistency.

The conventional deodorization apparatus using the microorganism-retaining carriers does not operate properly and there is a case where adequate deodorization cannot be performed, depending on an ammonia concentration and flow rate of the odorous gas discharged from the facilities, and situations of various operating environments (outside air temperature and pH of circulating water). Further, it is not possible to appropriately monitor a state of the deodorization apparatus, and it is difficult to grasp a timing and contents of maintenance.

According to an embodiment of the present invention, it is possible to solve the problems described above and other problems described in the following sentences.

First Embodiment

Hereinafter, an embodiment of the present invention will be described with reference to the drawings. FIG. 1 is a diagram showing a configuration of a deodorization treatment apparatus according to an embodiment of the present invention.

[Overall Configuration]

The deodorization treatment apparatus 100 is connected to a facility 200 emitting the odorous gas. The facility 200 emits the odorous gas containing a high ammonia concentration or the like and exhibiting a strong offensive odor. Specific examples of the facility include a composting treatment facility and a drainage treatment facility, but other facilities may be if the facilities emit offensive odors. The odorous gas discharged from the facility 200 is supplied to the deodorization treatment apparatus 100 by a gas pipe 151.

The gas pipe 151 is formed of a material having pressure resistance and corrosion resistance, for example, a material such as metal, vinyl chloride, or the like, and is formed in a pipe shape, a tube shape, or a hose shape capable of allowing a gas to pass therethrough. As will be described later, a blower 152 for increasing air volume, gas flow resistance regulators 153 and 155 for controlling the air volume, and a cooling device 154 for cooling the odorous gas are arranged in a middle of the gas pipe 151.

[Configuration of Treatment Apparatus]

The deodorization treatment apparatus 100 is arranged with a treatment apparatus including a deodorant tank 110, a water sprinkler device 120, a drainage tank 130, and a water tank 140. Among them, an odor of the odorous gas is removed by the microorganisms immobilized to microorganism-retaining carriers filled in the deodorant tank 110.

[Configuration of Deodorant Tank]

The deodorant tank 110 is, for example, a rectangular parallelepiped container having a height of 8 meters, width and length of 9 meters×12 meters, respectively. The deodorant tank is made of a material having high pressure resistance and high corrosion resistance, for example, metal, hard resin, reinforced concrete, or the like.

At a lower part of the deodorant tank 110, a port connected to the gas pipe 151 for taking in the odorous gas is arranged, and a space such that the odorous gas spreads over the entire in plain view is arranged. It is desirable to secure the space by covering a pallet or the like formed of a skeleton having a height of 20 cm to 40 cm or the like. It is preferable that a mesh-like sheet or plate is arranged on the pallet to prevent the microorganism-retaining carriers from flowing out to the drainage tank 130.

[Microorganisms and Microorganism-Retaining Carriers]

An inside of the deodorant tank 110 is filled with a microorganism-retaining carriers. Ammonia-degrading microorganisms and hydrogen sulfide-degrading microorganisms are immobilized on the microorganism-carrying carrier. The ammonia-degrading microorganisms are microorganisms that degrade ammonia dissolved in water or convert it into another substance. Exemplary ammonia-degrading bacteria include nitrifying bacteria. The nitrifying bacteria nitrify dissolved ammonia and convert it into nitrous acid or nitric acid. Here, nitrification refers to an oxidative decomposition of ammonia. Examples of nitrifying bacteria include ammonia oxidizing bacteria and nitrite oxidizing bacteria, the former convert ammonia into nitrous acid and the latter convert nitrous acid into nitric acid. In this way, ammonia of the odorous gas is decomposed and the odor is removed. The hydrogen sulfide-degrading microorganisms are microorganisms that decompose hydrogen sulfide dissolved in water or convert it into another substance. Exemplary hydrogen sulfide-degrading bacteria include sulfur bacteria. The sulfur bacteria decompose dissolved hydrogen sulfide into water and sulfur. The gas from which the odor has been removed in this way is discharged to the outside from an upper part of the deodorant tank 110.

The microorganism-retaining carrier is preferably a porous glass, but is not particularly limited if it can appropriately retain microorganisms. For example, in addition to glass, synthetic resin foam (foamed propylene), wood, ceramic, or the like may be used, and the shape thereof may be spherical, irregular shape, honeycomb shape, cylindrical shape, or the like.

As an example of the microorganism-retaining carriers, it is desirable to use porous glass grains having a size of, for example, several millimeters to several centimeters in diameter. It is desirable that the diameter of the pores of the glass grains are, for example, on the order of several micrometers to several millimeters, and have a surface area of several square meters or more and several tens of square meters or less per gram. The ammonia-degrading microorganisms and the hydrogen sulfide-degrading microorganisms inhabit these pores.

The odorous gas is taken in from the lower part of the deodorant tank 110, and as the odorous gas slowly rises in the deodorant tank 110, the odor is removed by the microorganisms living in the microorganism-retaining carriers. Then, the gas from which the odor has been removed is discharged from the upper part of the deodorant tank 110 to the outside.

[Configuration of Water Sprinkler Device]

The water sprinkler device 120 is arranged at the upper part of the deodorant tank 110. It is composed of a water supply pipe in which multiple water nozzles 121 are arranged. The water supply pipe sucks the treat water from the water tank 140 by a pump 122. Although the treat water is water, various agents such as phosphoric acid may be included in order to adjust pH and adjust the activity environment of the microorganism. The treat water contains air bubbles generated in liquid by an aeration device 142 described later.

The treat water sprayed from the multiple water sprinkler nozzles 121 of the water sprinkler device 120 is used for promoting growth and activity of microorganisms inhabiting the microorganism-retaining carriers. The treat water descended from the deodorant tank flows into the water tank 140 via the drainage tank 130 and the drain recovery pipe 141, and the treat water is stored again. In this way, the treat water is circulated and used in the deodorization treatment apparatus 100.

It is desirable to change amount and frequency of the treat water sprinkled by the water sprinkler device 120 in accordance with air temperature or the like in order to grow microorganisms. In addition, the microorganisms living in the microorganism-retaining carriers generate heat during their activities, and the treat water deprives the heat and cools the microorganisms. Therefore, for example, in the summer when the temperature is high, it is desirable to increase the number of times of water sprinkling and amount of water sprinkling each time. Specifically, it is desirable to increase the number of times of water sprinkling, such as sprinkling water for about 5 minutes in one hour in winter and sprinkling water for about 5 minutes in 30 minutes in summer.

[Configuration of Drainage Tank]

The drainage tank 130 is a tank for recovering the treat water descended from the deodorant tank 110. A drainage drain is arranged at a central portion or one end of a bottom of the drainage tank 130, and the bottom of the drainage tank 130 is inclined by about 2 degrees toward the drainage drain. However, the present invention is not limited thereto, and the bottom portion of the drainage tank 130 may be, for example, inclined by one degree or more toward the drainage drain. The drainage drain is arranged with a basket for receiving the microorganism-retaining carriers that has passed through the mesh. The treat water discharged from the drainage drain flows into the water tank 140 via the drain recovery pipe 141.

[Configuration of Water Tank]

The water tank 140 stores the recovered treat water. The water tank 140 is arranged with an aeration device 142 so that the treat water contains a high concentration of air, in particular oxygen. The aeration device 142 may be, for example, a microbubble generation device. In this case, the microbubble generation device may generate microbubbles containing oxygen in the treat water. The treat water stored in the water tank 140 is supplied to the water sprinkler device by the pump 122. The water tank 140 may further include a water supply pipe via the drain valve 143, a water supply pipe via the water supply valve 144, and a spraying device 145. Each of the drain valve 143 and the water supply valve 144 is a solenoid valve, and the operation thereof is controlled by a control device 160, which will be described later, together with the pump 122. The operation of the spraying device 145 is controlled by the control device 160, which will be described later. In FIG. 1, the deodorization treatment apparatus 100 is a treatment apparatus comprising of one deodorant tank 110, one water sprinkler device 120, one drainage tank 130, and one water tank 140. However, without being limited thereto, the treatment apparatus may be configured such that two deodorant tanks 110 are connected to each other, and in this case, two water tanks 140 may be provided. The two water tanks 140 may exchange water with each other.

[Configuration of Supply Path of Odorous Gas]

The odorous gas discharged from the facility 200 is supplied to the deodorization treatment apparatus 100 by the gas pipe 151. The blower 152 for supplying an odorous gas from the facility 200 to the gas pipe 151, the gas flow resistance regulators 153 and 155 for controlling the air volume, and the cooling device 154 for cooling the odorous gas are arranged in the middle of the gas pipe 151. A demister or the like for dehumidifying and dedusting may be further arranged between the facility 200 and the blower 152. The demister may be, for example, a sponge-like material that separates foreign matters such as liquid particles and dust contained in the odorous gas.

The blower 152 increases the flow rate of the odorous gas discharged from the facility 200. A negative pressure is generated on a suction side (left side in the drawing) and a positive pressure is generated on an exhaust side (right side in the drawing) of the blower 152. The blower is controlled by an inverter, and number of revolutions can be continuously controlled. By controlling the number of revolutions, the air volume and the air pressure can be controlled. Whether or not the operation is performed and the number of revolutions of the blower 152 are controlled by the control device 160.

The odorous gas discharged from the facility 200 is relatively hot. It may exceed 70° C. depending on the temperature and operating conditions of the facility. Only passing through the gas pipe 151 has some cooling effect, but this is insufficient, and the odorous gas is cooled by the cooling device 154. As a result, the odorous gas becomes 40° C. or less at the output side of the cooling device 154. The configuration of the cooling device may include, for example, a configuration in which the odorous gas is passed through a radiator in which many water pipes are arranged and cooling water circulates, and a configuration in which the odorous gas is directly cooled by sprinkling water into the cavity, and the like. Cooling capacities can be adjusted by changing a circulation speed of the cooling water in the former case, and can be adjusted by changing watering amount in the latter case. The operation is controlled by the control device 160.

The gas flow resistance regulators 153 and 155 are arranged on an input side and an output side of the cooling device 154, respectively. The gas flow resistance regulators 153 and 155 may be, for example, gas dampers. The gas flow resistance regulators 153 and 155 can adjust the resistance of the flow of the odorous gas by rotating movable valves to reduce the flow rate of the odorous gas. The gas flow resistance regulators 153 and 155 can also cool and dilute the odorous gas by opening and closing air supply ports that lead to outside air. Adjustment of opening/closing angle of the movable valve (adjustment of the flow resistance) and adjustment of opening/closing of the air supply port are performed by a motor, and the control is performed by the control device 160.

[Sensor Group]

The deodorization treatment apparatus 100 includes sensors 171, 172, 173, 174, 175, 176, 177, 178, and 179. Although the values measured by these sensors vary, the sensors 171, 172, 173, 174 measure any or more of the flow rate of the odorous gas, the ammonia concentration, the temperature, or the amount of dust, or pressure in the pipe. The sensor 175 measures one or more of the flow rates, the ammonia concentration, or the temperature of the gas discharged outdoors. The sensor 176 measures any one or more of the pressures, the ammonia concentration, or the pressure inside the deodorant tank 110. The sensor 177 measures the flow rate of the treat water in the drain recovery pipe 141, and the sensor 178 measures any one or more of the pH, the temperature, the ammonia concentration, the NO concentration, the $NO_2$ concentration, the dissolved oxygen concentration, electric conductivity, and the water level of the treat water stored in the water tank 140. The sensor 179 measures the flow rate of the treat water in the water supply pipe between the pump 122 and the water sprinkler nozzle 121. The measured values of these sensors are then sent to the control device 160. Further, the drain of the drainage tank 130 may be arranged with an outflow microorganism-retaining carrier basket (not shown) for receiving the microorganism-retaining carrier that has passed through the mesh, and a sensor for measuring weight of the outflow microorganism-retaining carrier basket or amount of outflow microorganism-retaining carriers in the basket.

Due to the nature of the deodorization treatment, the sensors 171, 172, 173, 174, 175, 176, 177, 178, and 179 do not have to be continuously measured, for example, once an hour, once every 6 hours, once a day. However, it is desirable to increase measurement frequency in the case where an urgent response (alert) is approached. For example, a case where the temperature of the deodorant tank 110 being elevated is detected by the sensor 176, a case where the ammonia concentration of the exhaust gas becomes equal to or higher than a predetermined value is detected by the sensor 175, a case where the water level of the water tank 140 becomes equal to or lower than a predetermined value, a case where the temperature of the odorous gas supplied to the deodorant tank 110 is equal to or higher than a predetermined temperature is detected by the sensor 174, and a case where clogging of the water sprinkler nozzle 121 is detected by the sensor 179, and the like. In addition, it may be a case where the weight of the outflow microorganism-retaining carrier basket or the amount of the microorganism-retaining carrier in the basket is detected to be equal to or larger than a predetermined value. In such cases, the measurement frequency is increased when the first threshold value is exceeded, and an alarm is issued when the second threshold value is exceeded.

[Controller]

The deodorization treatment apparatus 100 is arranged with the control device 160. The control device 160 is a microcontroller and includes a CPU and a storage device (not shown).

The measured values transmitted from the sensors 171, 172, 173, 174, 175, 176, 177, 178, and 179 are temporarily stored in the storage device in the control device 160. Then, the control device 160 controls any or more of the amount of air blowing of the blower 152, the watering amount or the watering frequency of the water sprinkler device 120 (controlling a pumping timing and pumping amount of the pump 122, and controlling the amount of the water sprinkler nozzle 121 used by a solenoid valve (not shown)), the cooling capacity of the cooling device 154, the opening degree of the gas flow resistance regulator 153 and 155, the amount of air bubbles generated in liquid of the aeration device 142, the water supply and drainage to the water tank 140 (water supply and drainage are performed by opening and closing the drain valve 143 and the water supply valve 144), the spraying of the mist to the water tank 140, the temperature of the deodorant tank 110 (raising the temperature by operating a heater (not shown)). A part indicated by the dotted arrows in the figure respectively shows a transmission path of the measured value (data) from the sensors 171, 172, 173, 174, 175, 176, 177, 178, and 179 to the control device 160, and the transmission path of the control signal from the control device 160 to the blower 152, the water sprinkler device 120, the cooling device 154, the gas flow resistance regulators 153 and 155, the aeration device 142, the drain valve 143 and the water supply valve 144, and the spraying device 145 (only a part is shown).

The control device 160 includes a communication device 161. The measured values transmitted from the sensors 171, 172, 173, 174, 175, 176, 177, 178, and 179 are taken into the storage device in the control device 160 temporarily, and the communication device 161 transfers the acquired measured values (data) to a remote server. The communication device 161 wirelessly communicates with base stations using, for example, a 4G network or a 5G network.

[Various Control Modes]

The control device 160 controls any or more of the amount of air blowing of the blower 152, the watering amount or the watering frequency of the water sprinkler device 120, the cooling capacity of the cooling device 154, the opening degree of the gas flow resistance regulators 153 and 155, the amount of the air bubbles generated in liquid of the aeration device 142, the water supply and the drainage to the water tank 140, the spraying of the mist to the water tank 140, and the temperature of the deodorant tank 110 by operating a corresponding control mode by operating a program that implements the following algorithms based on the measured values transmitted from the sensors 171, 172, 173, 174, 175, 176, 177, 178, and 179. Detailed description will be given below.

[Control Mode 1 (Temperature Control 1)]

When the temperature of the supplied odorous gas exceeds 40° C., the activity amount of nitrifying bacteria in the deodorant tank 110 decreases. Therefore, proper temperature control is required. First, the temperature of the odorous gas at the point of supplying the odorous gas to the deodorant tank 110 is measured by a temperature sensor in the sensor 174. Then, the temperature takes a constant margin from 40° C. is a control temperature, for example, exceeds 35° C., to reduce the amount of air blowing by controlling the inverter of the blower 152 (for example, lowering the number of revolutions). In the case where the temperature of the odorous gas supply port of the deodorant tank 110 is not sufficiently lowered even if the amount of air blowing is reduced, then the resistance of the flow of the gas flow resistance regulator 155 is increased (the valve is rotated from the open side to the closed side). The gas flow resistance regulator 155 may be operated more strictly by comparing pressures at its input side and output side with measured values of a pressure sensor contained in the sensors 173 and 174. If the amount of air blowing is reduced only by the control of the blower 152, although there is a possibility that a resistance of a flow of the cooling device 154 is lost, if the supply amount of the odorous gas to the odorous gas supply port is controlled in combination with not only the blower 152 but also the gas flow resistance regulator 155, the operation of the cooling device 154 is not stopped. In this way, even if the temperature of the odorous gas supplied from the facility 200 changes according to the outside air or a situation of the facility 200, it is always possible to operate the deodorization treatment apparatus with high efficiency.

[Control Mode 2 (Temperature Control 2)]

First, the temperature of the odorous gas at the point of supplying the odorous gas to the deodorant tank 110 is measured by the temperature sensor in the sensor 174. In the case where the temperature exceeds, for example, 35° C., the capacity of the cooling device 154 is improved. For example, if the cooling device 154 in which many water pipes are arranged and cooling water circulates is a radiator system, the circulation speed of the cooling water is increased, and if the cooling device is a system in which the odorous gas is directly cooled by watering in the cavity, the capacity can be improved by increasing the watering amount. A control mode 2 is preferably used in combination with the control mode 1. In this way, even if the temperature of the odorous gas supplied from the facility 200 changes according to the outside air or the situation of the facility 200, it is always possible to operate the deodorization treatment apparatus with high efficiency.

[Control Mode 3 (Control by Ammonia Concentration of Odorous Gas)]

The nitrifying bacteria in the deodorant tank 110 lower decomposition efficiency when the ammonia concentration of the supplied odorous gas becomes equal to or higher than a certain level. Therefore, the ammonia concentration in the odorous gas at the point of supplying the odorous gas to the deodorant tank 110 is measured by an ammonia concentration sensor in the sensor 174. As the ammonia concentration sensor, a laser sensor that measures the concentration by a degree of absorption of the laser and a high-frequency sensor that supplies a high frequency between electrodes and measures the concentration by a degree of resonance thereof, and the like can be used. In the case where the ammonia concentration in the odorous gas at the point of supplying the odorous gas to the deodorant tank 110 exceeds an appropriate concentration that can be processed in the deodorant tank 110, the inverter of the blower 152 is controlled to reduce the amount of air blowing. In the case where the ammonia concentration does not sufficiently decrease even if the amount of air blowing decreases, the resistance of the flow of the gas flow resistance regulator 155 is subsequently increased. In this way, even if the ammonia concentration of the odorous gas supplied from the facility 200 increases, it is possible to always operate the deodorization treatment apparatus with high efficiency.

[Control Mode 4 (Control by Emission Ammonia Concentration 1)]

The fact that the ammonia concentration of the gas discharged from the deodorant tank 110 is equal to or higher than a certain value means that the deodorant tank 110 is operating at a high load that exceeds its capacity. Therefore, the ammonia concentration of the gas discharged from the deodorant tank 110 is measured by an ammonia concentration sensor in the sensor 175. In the case where the ammonia concentration in the exhaust gas exceeds an environmental standard or other set value, the inverter of the blower 152 is controlled to reduce the amount of air blowing. In the case where the ammonia concentration in the exhaust gas does not sufficiently decrease even if the amount of air blowing decreases, the resistance of the flow of the gas flow resistance regulator 155 is subsequently increased. In this way, even if the ammonia concentration of the odorous gas supplied from the facility 200 increases, it is possible to always operate the deodorization treatment apparatus with high efficiency.

[Control Mode 5 (Control by Emission Ammonia Concentration 2)]

As described above, the fact that the ammonia concentration of the gas discharged from the deodorant tank 110 is equal to or higher than a certain value means that the deodorant tank 110 is operating at a high load that exceeds its capacity. As a cause thereof, there is a possibility that activity amount of the microorganisms immobilized to the microorganism-retaining carriers in the deodorant tank 110 is reduced. The reason for the decrease in the activity of microorganisms may be due to the temperature described above. Therefore, the temperature is lowered by the control mode 1 or 2 and the combination thereof. In this way, it is possible to prevent the deodorization treatment apparatus from being overloaded.

[Control Mode 6 (Control by Emission Ammonia Concentration 3)]

As described above, the fact that the ammonia concentration of the gas discharged from the deodorant tank 110 is equal to or higher than a certain value means that the deodorant tank 110 is operating at a high load that exceeds its capacity. As a cause thereof, there is a possibility that the treat water sprayed on the microorganism-retaining carriers in the deodorant tank 110 is insufficient, and as a result, the activity amount of the immobilized microorganism is reduced. Therefore, in the case where the measured value of the ammonia concentration sensor of the sensor 175 is equal to or higher than the predetermined value, the pump 122 can be controlled to increase the watering amount or increase the watering frequency, and the number of nozzles used by operating a solenoid valve (not shown) can be increased to increase the watering amount. In this way, it is possible to prevent the deodorization treatment apparatus from being overloaded.

[Control Mode 7 (Control by Emission Ammonia Concentration 3)]

As described above, the fact that the ammonia concentration of the gas discharged from the deodorant tank 110 is equal to or higher than a certain value means that the deodorant tank 110 is operating at a high load that exceeds its capacity. As a cause thereof, there is a possibility that the oxygen concentration in the treat water sprayed to the microorganism-retaining carriers in the deodorant tank 110 is insufficient, and as a result, the activity amount of the immobilized microorganisms is lowered. Therefore, in the case where the measured value of the ammonia concentration sensor of the sensor 175 is equal to or higher than the predetermined value, the aeration device 142 can be operated to apply more oxygen to the treat water. In this way, it is possible to prevent the deodorization treatment apparatus from being overloaded.

[Control Mode 8 (Control by Temperature in Deodorant Tank 1)]

A reason for the decrease in the activity amount of the microorganisms may be due to the temperature in the deodorant tank 110 described above. In the case where the measured value of the temperature sensor of the sensor 176 exceeds a predetermined value, for example 50° C., the pump 122 is controlled to increase the watering amount or increase the watering frequency, and the number of nozzles used by operating a solenoid valve (not shown) can be increased to increase the watering amount. Cooling progresses as the amount of water sprinkled increases. In this way, it is possible to prevent the deodorization treatment apparatus from being overloaded.

[Control Mode 9 (Control by Temperature in Deodorant Tank 2)]

As described above, a reason for the decrease in the activity amount of the microorganisms may be due to the temperature in the deodorant tank 110 described above. Then, in the case where the measured value of the temperature sensor of the sensor 176 exceeds a predetermined value, for example 50° C., the temperature is lowered by the control mode 1 or 2 and the combination thereof. In this way, it is possible to prevent the deodorization treatment apparatus from being overloaded.

[Control Mode 10 (Control by Measurement Result of Treat Water)]

In the deodorization treatment apparatus 100, the treat water is circulated and used. When the thermometer of the sensor 178 indicates a temperature equal to or higher than a predetermined value, the water supply valve 144 is opened to supply water to the water tank, or mist is sprayed to the water tank by the spraying device 145. The spraying of the mist by the spraying device 145 also contributes to the removal of dust in the water tank. In the case where a water level gauge of the sensor 178 indicates a water level drop in the water tank 140, the water supply valve 144 is opened to supply water. In the case where the water level gauge of the sensor 178 indicates an increase in the water level of the water tank 140, the drain valve 143 is opened to drain the water. In the case where a pH sensor of the sensor 178 indicates a value outside a predetermined value range, and in the case where a dissolved ammonia sensor, an NO sensor, an $NO_2$ sensor, an electric conductivity sensor, and a dissolved oxygen concentration sensor indicate a value outside the predetermined range, the drain valve 143 is opened to drain the water and the water supply valve 144 is opened to supply new water. In this way, it is possible to prevent the treated water from becoming inappropriate for the activity of microorganisms or malfunctioning due to the water scale attached to the pipe.

[Information Collection System in Remote Location]

Figure 2:
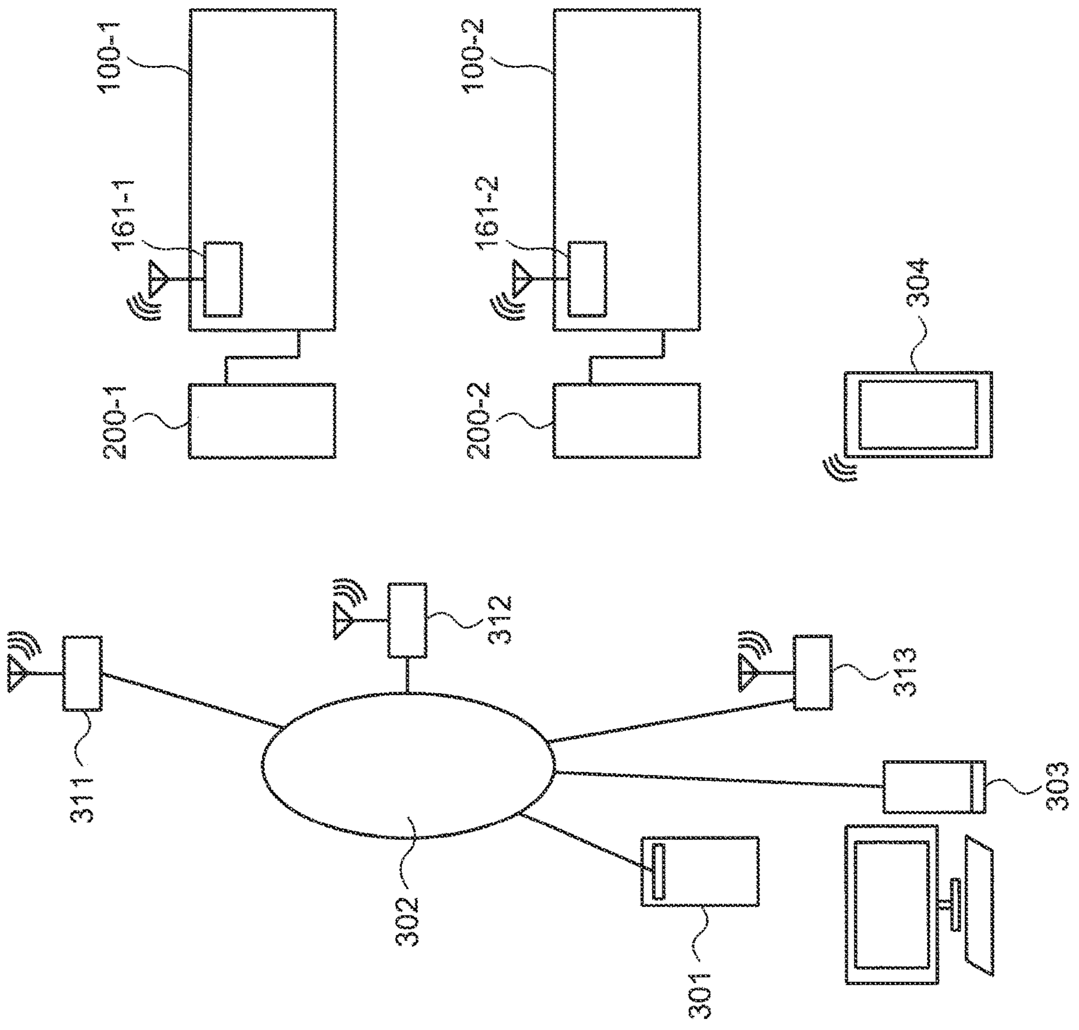
FIG. 2 is a diagram showing a deodorization treatment apparatus being connected to a communication network according to an embodiment of the present invention.

FIG. 2 is a diagram of a deodorization treatment apparatus connected by a communication network according to an embodiment of the present invention. The combinations of the facility 200 emitting odorous gas and deodorization treatment apparatuses 100 are arranged in multiple regions (a facility 200-1 and a deodorization treatment apparatus 100-1 are arranged in one region, and a facility 200-2 and a deodorization treatment apparatus 100-2 are arranged in another region. The number of regions may be larger). The communication device 161 arranged in the deodorization treatment apparatus 100 (a communication device 161-1 is arranged in the deodorization treatment apparatus 100-1 of one region, a communication device 161-2 is arranged in the deodorization treatment apparatus 100-2 of another region, respectively.) wirelessly communicates with base stations 311 and 312 using, for example, a 4G or a 5G network. The base stations 311 and 312 are connected to a wireless user terminal 304 via a server 301, a user terminal 303, and another base station 313 via an internet 302.

The server 301 receives the measured values (data) transmitted from the sensors 171, 172, 173, 174, 175, 176, 177, 178, and 179 from the communication devices 161-1 and 161-2, and stores them in the storage device therein. Frequency of loading the measured value (data) into the server 301 may be performed at intervals of, for example, once an hour, once a day, once a week, or may be performed according to instructions from user terminals 303 and 304. The captured data may be one measured value or multiple measured values (for example, in the case where 24 data measured once per hour are transmitted once a day).

A web server is running on the server 301, and the measured values obtained by this web server are displayed on the browser screens of the user terminals 303 and 304. It is desirable to be able to understand hourly or daily transitions by displaying a graph. In addition, various measured values for each region may be displayed on one web page, and various measured values corresponding to multiple regions may be superimposed on one graph. In this way, it becomes possible to manage the deodorization treatment apparatuses of multiple regions in a unified manner, and it is possible to compare and examine the operation statuses.

[Communication not Via Server]

In the above example, the measured values collected via the server 301 are browsed by the user terminals 303 and 304, but the software (applet (app) in the case of a smartphone terminal) installed in the user terminals 303 and 304 may directly receive the measured values (data) from the communication devices 161-1 and 161-2.

[Alerts with Outliers]

In the case where the response requires urgency (alert), such as the case where the measured values (data) transmitted from the sensors 171, 172, 173, 174, 175, 176, 177, 178, and 179 indicate outliers, the data may be push-transmitted to the server 301 at the initiative of the control device 160. In this case, emergency information (alerting information) may be transmitted to the user terminals 303 and 304 at the same time by using an SMS or an e-mail protocol. Administrators of the system operating the user terminals 303 and 304 can immediately take immediate action at the site. The case requiring urgency, for example, a case where the temperature of the deodorant tank 110 is rapidly increased is detected by the sensor 176, a case where the ammonia concentration of the exhaust gas is a predetermined or more is detected by the sensor 175, a case where the water level of the water tank 140 is not recovered even after the water supply valve 144 is opened to supply water when the water has fallen below a predetermined level is detected by the sensor 178, a case where the sensor 174 detects that the temperature of the odorous gas supplied to the deodorant tank 110 is above a predetermined temperature, and a case where the weight of the outflow microorganism-retaining carrier basket or the amount of the microorganism-retaining carriers in the basket is equal to or larger than a predetermined value is detected, and the like.

[Maintenance Alert]

A dust amount sensor included in any of the sensors 171, 172, 173, or 174 may periodically measure dust amount of the odorous gas, and when the integrated amount exceeds a predetermined value, the server 301 may generate a maintenance alert to the user terminals 303 and 304.

[Control of Deodorization Treatment Apparatus from Remote Location]

It is possible to manage operating states of the deodorization treatment apparatuses 100-1 and 100-2 on the user terminals 303 and 304 by using the above-described system. The user terminals 303 and 304 may be configured to transmit instructions to the communication devices 161-1 and 161-2 via the server 301 or directly to control any or more of the amount of air blowing of the blower 152, the watering amount or the watering frequency of the water sprinkler device 120, the cooling capacity of the cooling device 154, the opening degree of the gas flow resistance regulators 153 and 155, the amount of the air bubbles generated in liquid of the aeration device 142, the water supply and drainage to the water tank 140, and the temperature of the deodorant tank 110.

Second Embodiment

Figure 3:
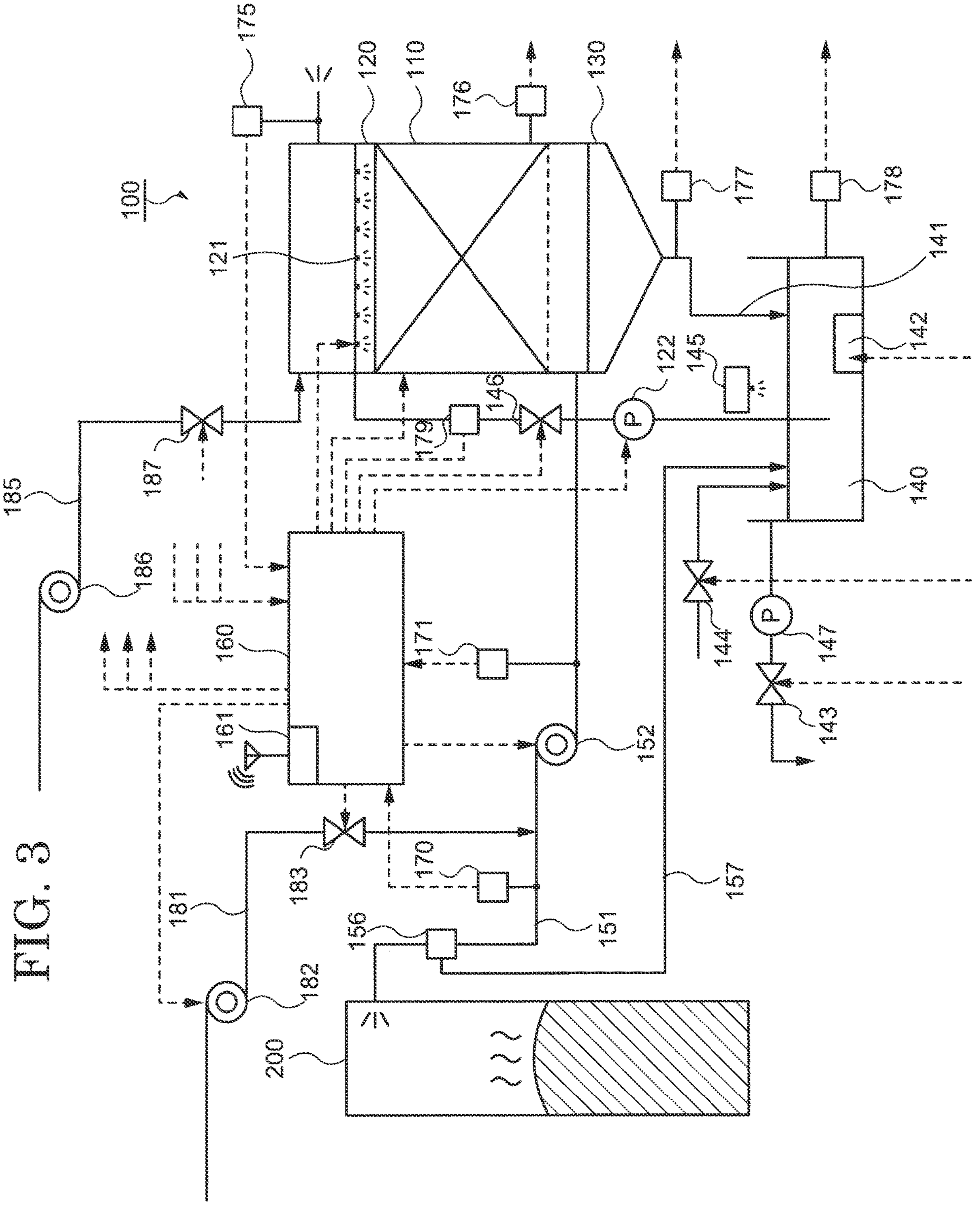
FIG. 3 is a diagram showing a configuration of a deodorization treatment apparatus according to an embodiment of the present invention.

FIG. 3 is a diagram showing a configuration of a deodorization treatment apparatus according to an embodiment of the present invention. The configuration of the deodorization treatment apparatus according to the second embodiment is same as the configuration of the deodorization treatment apparatus according to the first embodiment except having a second blower instead of the cooling device, and further including a third blower and a demister. Descriptions that are same as those in the first embodiment are omitted, and the different parts from the configuration of the deodorization treatment apparatus according to the first embodiment will be described here.

[Overall Configuration]

A deodorization treatment apparatus 100*a* is connected to the facility 200 emitting the odorous gas. The odorous gas discharged from the facility 200 is supplied to the deodorization treatment apparatus 100 by the gas pipe 151. As will be described later, a demister 156 and the first blower 152 for increasing the air volume are arranged in the middle of the gas pipe 151. The demister 156 filters the odorous gas discharged from the facility 200 to perform dehumidification and dust removal. Condensation (drainage) discharged by the demister 156 flows into the water tank 140 via a drain recovery pipe 157. Further, a pipe 181 is connected between the demister 156 and the first blower 152, which is arranged with a second blower 182 that takes in outside air and dilutes the odorous gas discharged from the facility 200.

[Configuration of Treatment Apparatus]

The deodorization treatment apparatus 100 is arranged with the treatment apparatus including the deodorant tank 110, the water sprinkler device 120, the drainage tank 130, and the water tank 140. Among them, the odor of the odorous gas is removed by the microorganisms immobilized to the microorganism-retaining carriers filled in the deodorant tank 110. The configuration of the deodorant tank 110, the water sprinkler device 120, and the drainage tank 130 according to the present embodiment is the same as the configuration of the deodorant tank 110, the water sprinkler device 120, and the drainage tank 130 according to the first embodiment, and thus description thereof will be omitted.

The odorous gas is taken in from the lower part of the deodorant tank 110, and as the odorous gas slowly rises in the deodorant tank 110, the odor is removed by the microorganisms living in the microorganism-retaining carriers. Then, the gas from which the odor has been removed is discharged from the upper part of the deodorant tank 110 to the outside. In the upper part of the deodorant tank 110, a port connected to a pipe 185 for taking in the outside air is provided, and a space for further diluting the gas from which the odor has been removed with the outside air is provided. The pipe 185 is arranged with a third blower 186 that blows outside air.

The water sprinkler device 120 is arranged at the upper part of the deodorant tank 110. It is composed of a water supply pipe in which multiple water nozzles 121 are arranged. The water supply pipe sucks the treat water from the water tank 140 by the pump 122. The treat water descended from the deodorant tank flows into the water tank 140 via the drainage tank 130 and the drain recovery pipe 141, and the treat water is stored again. In this way, the treat water is circulated and used in the deodorization treatment apparatus 100.

The drainage tank 130 is a tank for recovering the treat water descended from the deodorant tank 110. The treat water discharged from the drainage drain flows into the water tank 140 via the drain recovery pipe 141.

The water tank 140 stores the recovered treat water. The water tank 140 is arranged with the aeration device 142 so that the treat water contains a high concentration of air, in particular oxygen. The treat water stored in the water tank 140 is supplied to the water sprinkler device by the pump 122 via a water supply valve 146. The water tank 140 may further include a water supply pipe via a pump 147 and the drain valve 143, a water supply pipe via the water supply valve 144, and the spraying device 145. Each of the drain valve 143, the water supply valve 144, and the water supply valve 146 is a solenoid valve, and the operation thereof is controlled by the control device 160, which will be described later, together with the pump 122 and the pump 147. The operation of the spraying device 145 is controlled by the control device 160, which will be described later. In FIG. 3, the deodorization treatment apparatus 100 is a treatment apparatus comprising of one deodorant tank 110, one water sprinkler device 120, one drainage tank 130, and one water tank 140. However, without being limited thereto, the treatment apparatus may be configured such that two deodorant tanks 110 are connected to each other, and in this case, two water tanks 140 may be provided. The two water tanks 140 may exchange water with each other.

[Configuration of Odorous Gas Supply Path]

The odorous gas discharged from the facility 200 is supplied to the deodorization treatment apparatus 100*a* by the gas pipe 151. The demister 156 for dehumidification and dust removal and the first blower 152 for supplying an odorous gas from the facility 200 to the gas pipe 151 are arranged in the middle of the gas pipe 151. The second blower 182 for blowing outside air and the pipe 181 arranged with an inlet valve 183 are further connected between the demister 156 and the first blower 152.

The first blower 152 increases the flow rate of the odorous gas discharged from the facility 200. The first blower 152 is controlled by the inverter, and number of revolutions can be continuously controlled. By controlling the number of revolutions, the air volume and the air pressure can be controlled. Whether or not the operation is performed and the number of revolutions of the first blower 152 are controlled by the control device 160.

The odorous gas discharged from the facility 200 is relatively hot. The odorous gas discharged from the facility 200 dilutes and cools the odorous gas by adding the outside air supplied by the second blower 182. The second blower 182 is controlled by an inverter so that the number of revolutions can be continuously controlled. By controlling the number of revolutions, the air volume and the air pressure can be controlled. Whether or not the operation is performed and the number of revolutions of the second blower 182 are controlled by the control device 160. The inlet valve 183 may be further arranged between the second blower 182 and the gas pipe 151. The inlet valve 183 is an electromagnetic valve, and its operation is controlled by the control device 160. The blowing amount of the outside air blown by the second blower 182 is, for example, preferably equal to or less than the blowing amount of the odorous gas discharged from the facility 200. As a result, the odorous gas becomes 40° C. or less on an input side of the first blower 152.

The third blower 186 dilutes the deodorized gas by adding more outside air. The third blower 186 is controlled by an inverter so that the number of revolutions can be continuously controlled. By controlling the number of revolutions, the air volume and the air pressure can be controlled. Whether or not the operation is performed and the number of revolutions of the third blower 186 are controlled by the control device 160. An inlet valve 187 may be further arranged between the third blower 186 and the upper part of the deodorant tank 110. The inlet valve 187 is an electromagnetic valve, and its operation is controlled by the control device 160.

[Sensor Group]

The deodorization treatment apparatus 100 includes sensors 170, 171, 175, 176, 177, 178, and 179. Although the values measured by these sensors vary, the sensors 170 and 171 measure any or more of the flow rate of the odorous gas, ammonia concentration, temperature, humidity or amount of dust, or pressure in the pipe. The sensor 175 measures one or more of the flow rates, the ammonia concentration, or the temperature of the gas discharged outdoors. The sensor 176 measures any one or more of the pressures, the ammonia concentration, the temperature, or the pressure inside the deodorant tank 110. The sensor 177 measures the flow rate of the treat water in the drain recovery pipe 141, and the sensor 178 measures any one or more of pH, the temperature, the ammonia concentration, the NO concentration, the $NO_2$ concentration, the dissolved oxygen concentration, the electric conductivity, and the water level of the treat water stored in the water tank 140. The sensor 179 measures the flow rate of the treat water in the water supply pipe between the pump 122 and the water sprinkler nozzle 121. The measured values of these sensors are then sent to the control device 160.

[Controller]

The deodorization treatment apparatus 100*a* is arranged with a control device 160. The control device 160 is a microcontroller and includes a CPU and a storage device (not shown).

The measured values transmitted from the sensors 170, 171, 175, 176, 177, 178, and 179 are temporarily stored in the storage device in the control device 160. Then, the control device 160 controls one or more of the amount of air blowing of the first blower 152, the amount of air blowing of the second blower 182, the amount of air blowing of the third blower 186, the watering amount or the watering frequency of the water sprinkler device 120 (controlling a pumping timing and pumping amount of the pump 122 and the water supply valve 146, and controlling the amount of the water sprinkler nozzle 121 used by a solenoid valve (not shown)), the amount of the air bubbles generated in liquid of the aeration device 142, the water supply to the water tank 140 and the drainage water (water supply and drainage are performed by controlling drainage timing and drainage amount of the pump 147, and opening and closing the water drain valve 143 and the water supply valve 144), the spraying of the mist to the water tank 140, and the temperature of the deodorant tank 110 (raising the temperature by operating a heater (not shown)). A part indicated by the dotted arrows in the figure respectively show the transmission paths of the measured value (data) from the sensors 170, 171, 175, 176, 177, 178, and 179 to the control device 160, and the transmission paths of the control signal from the control device 160 to the first blower 152, the second blower 182, the third blower 186, the water sprinkler device 120, the aeration device 142, the pump 147, the drain valve 143 and the water supply valve 144, and the spraying device 145 (only a part is shown).

The control device 160 includes a communication device 161. The measured values transmitted from the sensors 170, 171, 175, 176, 177, 178, and 179 are taken into the storage device in the control device 160 temporarily, and the communication device 161 transfers the acquired measured values (data) to a remote server. The communication device 161 wirelessly communicates with base stations using, for example, the 4G network or the 5G network.

[Various Control Modes]

The control device 160 controls any or more of the blowing amount of the first blower 152, the blowing amount of the second blower 182, the blowing amount of the third blower 186, the watering amount or the watering frequency of the water sprinkler device 120, the amount of the air bubbles generated in liquid of the aeration device 142, the water supply and drainage to the water tank 140, the spraying of mist to the water tank 140, and the temperature of the deodorant tank 110 by operating the corresponding control mode by operating a program that implements the following algorithms based on the measured values transmitted from the sensors 170, 171, 175, 176, 177, 178, and 179. Hereinafter, the same description as in the first embodiment will be omitted, and portions different from the control mode according to the first embodiment will be described in detail.

[Control Mode 1 (Temperature Control)]

When the temperature of the supplied odorous gas exceeds 40° C., the activity amount of the nitrifying bacteria in the deodorant tank 110 decreases. Therefore, proper temperature control is required. First, the temperature of the odorous gas at the point of supplying the odorous gas to the deodorant tank 110 is measured by a temperature sensor in the sensor 171. Then, the temperature takes a constant margin from 40° C. is a control temperature, for example, exceeds 35° C., to reduce the amount of air blowing by controlling the inverter of the first blower 152 (for example, lowering the number of revolutions). In the case where the temperature of the odorous gas supply port of the deodorant tank 110 is not sufficiently lowered even if the amount of air blowing is reduced, the inverter of the second blower 182 is controlled to increase the amount of air blowing of the outside air (for example, increasing the number of revolutions). The amount of air blowing of the outside air can be further strictly operated by the inlet valve 183. In this way, even if the temperature of the odorous gas supplied from the facility 200 changes according to the outside air or the situation of the facility 200, it is always possible to operate the deodorization treatment apparatus with high efficiency.

[Control Mode 2 (Control by Ammonia Concentration of Odorous Gas)]

The nitrifying bacteria in the deodorant tank 110 lower the decomposition efficiency when the ammonia concentration of the supplied odorous gas becomes equal to or higher than a certain level. Therefore, the ammonia concentration in the odorous gas discharged from the facility 200 is measured by an ammonia concentration sensor in the sensor 170. The ammonia concentration in the odorous gas at the point of supplying the odorous gas to the deodorant tank 110 is measured by an ammonia concentration sensor in the sensor 171. In the case where the ammonia concentration in the odorous gas discharged from the facility 200 exceeds an appropriate concentration that can be processed in the deodorant tank 110, the inverter of the first blower 152 is controlled to reduce the amount of air blowing. In the case where the ammonia concentration does not sufficiently decrease even if the amount of air blowing decreases, then the inverter of the second blower 182 is controlled to increase the amount of air blowing of the outside air. The amount of air blowing of the outside air can be further strictly operated by the inlet valve 183. In this way, even if the ammonia concentration of the odorous gas supplied from the facility 200 increases, it is possible to always operate the deodorization treatment apparatus with high efficiency.

[Control Mode 3 (Control by Emission Ammonia Concentration 1)]

The fact that the ammonia concentration of the gas discharged from the deodorant tank 110 is equal to or higher than a certain value means that the deodorant tank 110 is operating at a high load that exceeds its capacity. Therefore, the ammonia concentration of the gas discharged from the deodorant tank 110 is measured by the ammonia concentration sensor in the sensor 175. In the case where the ammonia concentration in the exhaust gas exceeds an environmental standard or other set value, the inverter of the first blower 152 is controlled to reduce the amount of air blowing. In the case where the ammonia concentration in the exhaust gas does not sufficiently decrease even if the amount of air blowing decreases, the inverter of the second blower 182 is controlled to increase the amount of air blowing of the outside air. In this way, even if the ammonia concentration of the odorous gas supplied from the facility 200 increases, it is possible to always operate the deodorization treatment apparatus with high efficiency.

[Control Mode 4 (Control by Emission Ammonia Concentration 2)]

As described above, the fact that the ammonia concentration of the gas discharged from the deodorant tank 110 is equal to or higher than a certain value means that the deodorant tank 110 is operating at a high load that exceeds its capacity. Therefore, the ammonia concentration of the gas discharged from the deodorant tank 110 is measured by the ammonia concentration sensor in the sensor 175. In the case where the ammonia concentration in the exhaust gas exceeds an environmental standard or other set value, the inverter of the third blower 186 is controlled to increase the amount of air blowing of the outside air. The ammonia concentration in the exhaust gas can be controlled to an environmental standard or other set value by diluting the gas discharged from the deodorant tank 110 with outside air. The ammonia concentration in the gas discharged from the deodorant tank 110 may be, for example, 50 ppm. In the case where an environmental standard value is 5 ppm, the environmental standard value can be satisfied by diluting the gas discharged from the deodorant tank 110 by 10 times.

[Control Mode 5 (Control by Emission Ammonia Concentration 3)]

As described above, the fact that the ammonia concentration of the gas discharged from the deodorant tank 110 is equal to or higher than a certain value means that the deodorant tank 110 is operating at a high load that exceeds its capacity. As a cause thereof, there is a possibility that the treat water sprayed on the microorganism-retaining carriers in the deodorant tank 110 is insufficient, and as a result, the activity amount of the immobilized microorganisms is reduced. Therefore, in the case where the measured value of the ammonia concentration sensor of the sensor 175 is equal to or higher than the predetermined value, the pump 122 can be controlled to increase the watering amount or increase the watering frequency, and the number of nozzles used by operating a solenoid valve (not shown) can be increased to increase the watering amount. The watering amount of the treat water can also be more strictly operated by the water supply valve 146. In this way, it is possible to prevent the deodorization treatment apparatus from being overloaded.

[Control Mode 6 (Control by Measurement Result of Treat Water)]

In the deodorization treatment apparatus 100, the treat water is circulated and used. When the thermometer of the sensor 178 indicates a temperature equal to or higher than a predetermined value, the water supply valve 144 is opened to supply water to the water tank, or mist is sprayed to the water tank by the spraying device 145. The spraying of the mist by the spraying device 145 also contributes to the removal of dust in the water tank. The temperature of the treat water is, for example, preferably 10° C. or more and 35° C. or less, and more preferably 10° C. or more and 30° C. or less. In the case where the water level gauge of the sensor 178 indicates a water level drop in the water tank 140, the water supply valve 144 is opened to supply water. In the case where the water level gauge of the sensor 178 indicates an increase in the water level of the water tank 140, the drain valve 143 is opened to drain the water. Drainage amount of the treat water can further control the pump 147 to increase the drainage amount or increase drainage frequency. In the case where the pH sensor of the sensor 178 indicates a value outside the predetermined value range, and in the case where the dissolved ammonia sensor, NO sensor, $NO_2$ sensor, the electric conductivity sensor, and the dissolved oxygen concentration sensor indicate a value outside the predetermined range, the drain valve 143 is opened to drain the water and the water supply valve 144 is opened to supply new water. The drainage amount of the treat water can further control the pump 147 to increase the drainage amount or increase the drainage frequency. pH of the treat water is, for example, preferably 6.5 or more and 8.5 or less, and more preferably 6.5 or more and 8.3 or less. In this way, it is possible to prevent the treated water from becoming inappropriate for the activity of microorganisms or malfunctioning due to the water scale attached to the pipe.

[Information Collection System in Remote Location]

Figure 4:
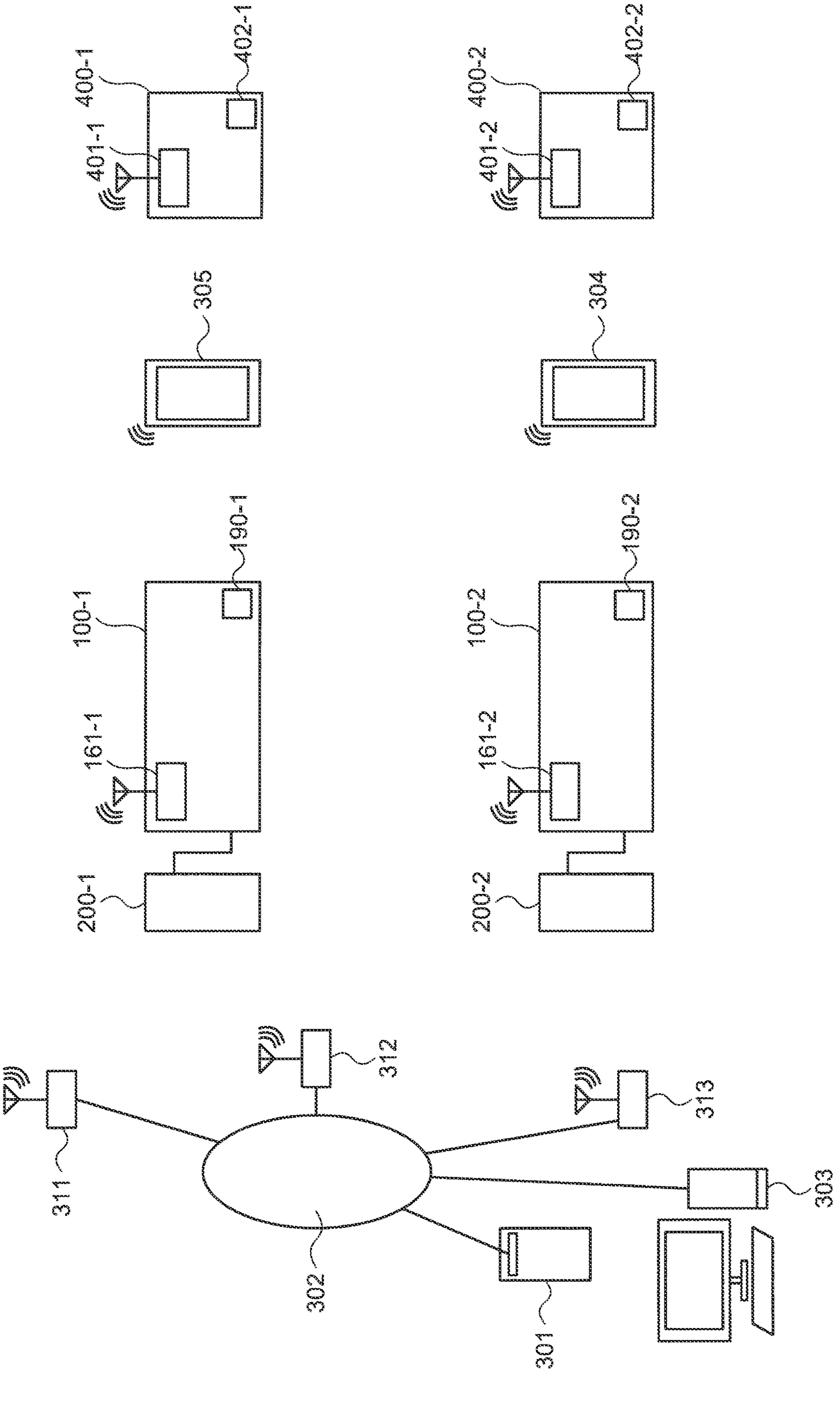
FIG. 4 is a diagram showing a deodorization treatment apparatus being connected to a communication network according to an embodiment of the present invention.

FIG. 4 is a diagram of a deodorization treatment apparatus connected by a communication network according to an embodiment of the present invention. Combinations of the facility 200 emitting odorous gas and the deodorization treatment apparatus 100 is arranged in multiple regions (the facility 200-1 and the deodorization treatment apparatus 100-1 are arranged in one region, and the facility 200-2 and the deodorization treatment apparatus 100-2 are arranged in another region. The number of regions may be larger). A sensor 190 arranged outside the deodorization treatment apparatus 100 (a sensor 190-1 is arranged in the deodorization treatment apparatus 100-1 in one area, and a sensor 190-2 is arranged in the deodorization treatment apparatus 100-2 in another area) measures, for example, any or more of the odors (not limited to ammonia), wind direction, atmospheric pressure, humidity, and temperature of the outside environment. The sensor 190 is preferably arranged in four different directions around the deodorization treatment apparatus 100. The communication device 161 arranged in the deodorization treatment apparatus 100 (communication device 161-1 in the deodorization treatment apparatus 100-1 in one region, and communication device 161-2 in the deodorization treatment apparatus 100-2 in another region are arranged respectively.) wirelessly communicates with the base stations 311 and 312 using, for example, the 4G or the 5G network.

Around the facility 200 and the deodorization treatment apparatus 100 emitting the odorous gas, a nearby institution 400 is arranged (the institution 400-1 is arranged in one area, the institution 400-2 is arranged in another area, the number of areas may be more). The nearby institution 400 is arranged at a location different from the facility 200 and the deodorization treatment apparatus 100 that emits the odorous gas. The location of the nearby institution 400 is not particularly limited, and is preferably arranged exhaustively. The form of the nearby institution 400 is not particularly limited. The nearby institution 400 may be an individual's house or may be a movable facility. A sensor 402 arranged outside of the institution 400 (a sensor 402-1 is arranged in the institution 400-1 in one area, and a sensor 402-2 is arranged in the institution 400-2 in another area) measures, for example, any or more of the odors (not limited to ammonia), wind direction, atmospheric pressure, humidity, and temperature in the outside environment. The sensors 402 are preferably arranged in four different directions around the institution 400. A communication device 401 arranged in the institution 400 (a communication device 401-1 is arranged in the institution 400-1 in one region, and a communication device 401-2 is arranged in the institution 400-2 in another region) wirelessly communicates with the base stations 311 and 312 using, for example, the 4G or the 5G network.

The base stations 311 and 312 are connected to wireless user terminals 304 and 305 via the server 301, the user terminal 303, and another base station 313 by the Internet 302. The user terminal 303 and the wireless user terminals 304 and 305 may be located at the location different from the facility 200 and the institution 400, and the deodorization treatment apparatus 100 that emit the odorous gas and may be located at a remote location.

The server 301 receives the measured values (data) transmitted from the sensors 190-1 and 190-2 from the communication devices 161-1 and 161-2, and stores them in the storage device therein. The server 301 receives the measured values (data) transmitted from the sensors 402-1 and 402-2 from the communication devices 401-1 and 401-2, and stores them in the storage device therein. The measured values (data) transmitted from the multiple sensors 190-1, 190-2, 402-1, and 402-2 include ID information for distinguishing the sensors and position information of the sensors. The frequency of loading the measured value (data) into the server 301 may be performed at intervals of, for example, once every 10 minutes, once every hour, once a day, once a week, or may be performed according to instructions from the user terminals 303 and 304. The captured data may be one measured value or multiple measured values (for example, a case where 24 data measured once per hour are transmitted once a day). The measured values (data) transmitted from the multiple sensors 190-1, 190-2, 402-1, and 402-2 are accumulated, and the correlations over time are analyzed by an AI, so that alerts associated with abnormal values described later, identification of sources of odors, and adjustment based on environmental factors can be performed.

A web server is running on the server 301, and the measured values taken in by web server are displayed on the browsers of the user terminals 303, 304, and 305. It is desirable to be able to understand hourly or daily transitions by displaying a graph. In addition, various measured values for each region and each sensor may be displayed on one web page, and various measured values corresponding to multiple regions may be superimposed on one graph. In this way, it is possible to collectively manage the odors in deodorization treatment apparatuses and nearby facilities of multiple regions.

[Communication not Via Server]

In the above example, the measured values collected via the server 301 are browsed by the user terminals 303, 304, and 305, but the software (applet (app) in the case of a smartphone terminal) installed in the user terminals 303, 304, and 305 may directly receive the measured values (data) from the communication devices 161-1, 161-2, 401-1, and 401-2.

[Alerts with Outliers]

In the case where urgency is required (alert), such as a case where the measured value (data) related to odor transmitted from the sensors 190-1, 190-2, 402-1, and 402-2 indicates an abnormal value, the data may be pushed to the server 301 under the initiative of the control device 160. In this case, the emergency information (alert information) may be transmitted to the user terminals 303, 304, and 305 at the same time by using a SMS or an e-mail protocol. The emergency information may include measured values of the sensor, ID information that distinguishes the sensor, and the position information of the sensor. The administrators of the system operating the user terminals 303, 304, and 305 can immediately act. For example, in the case where the sensor 190-1 detects an abnormal value exceeding a predetermined value, the administrators are possible to adjust the operation status of the deodorization treatment apparatus 100-1, and in the case where the sensor 402-1 also detects an abnormal value, the administrators are possible to further apologize to the person at the institution 400-1. Adjustment of the operation status of the deodorization treatment apparatus 100-1 may be carried out directly on-site or by remote control. The apology to the person at the institution 400-1 may be directly dealt with (apologized) in person, or may be returned to the facility in preset point or money.

[Identification of Sources of Odor]

Further, the server 301 can identify the source of the odor among the multiple deodorization treatment apparatuses 100-1 and 100-2 by correlating environmental factors such as the type, intensity, location, direction, wind direction, atmospheric pressure, humidity, and temperature of the odor transmitted from the multiple sensors 190-1, 190-2, 402-1, and 402-2. For example, even if an odor is not detected by the sensors 190-1 and 190-2, in the case where the sensor 402-2 detects an odor after the sensor 402-1, it is possible to specify that the source of the odor is the deodorization treatment apparatus 100-1 by correlating a movement and delay time of the odor detection place with environmental factors such as wind direction, atmospheric pressure, humidity, and temperature before and after the odor detection place. In this case, the emergency information transmitted to the user terminals 303, 304, and 305 may include information on the source of the odor.

[Adjustment Based on Environmental Factors]

Further, the server 301 is possible to prepare the operation status of the deodorization treatment apparatus 100 based on environmental factors such as the type, intensity, location, direction, wind direction, atmospheric pressure, humidity, and temperature of the odor transmitted from the multiple sensors 190-1, 190-2, 402-1, and 402-2. For example, since it is easy to smell odors when the air pressure in an area is low or the humidity and temperature are high, it is possible to adjust the operating conditions of the deodorization treatment apparatus 100 in that area.

[Control of Deodorization Treatment Apparatus from Remote Location]

By using the system described above, it is possible to manage the operating states of the deodorization treatment apparatuses 100-1 and 100-2 on the user terminals 303, 304, and 305. The user terminals 303, 304, and 305 may be configured to transmit instructions to the communication devices 161-1 and 161-2 via the server 301 or directly to control any or more of the amount of air blowing of the first blower 152, the amount of air blowing of the second blower 182, the amount of air blowing of the third blower 186, the watering amount or the watering frequency of the water sprinkler device 120, the amount of the air bubbles generated in liquid of the aeration device 142, the water supply and drainage to the water tank 140, and the temperature of the deodorant tank 110 according to the instruction from the user.

While an embodiment of the present invention has been described with reference to the drawings, it is needless to say that various modifications can be made without departing from the spirit of the invention.

According to an embodiment of the present invention, the deodorization apparatus can operate properly and perform sufficient deodorization even if there is a variation in the concentration and the flow rate of the ammonia of the odorous gas discharged from the facilities, or the situation of various operating environments. Further, it is possible to grasp the timing and contents of maintenance by appropriately monitoring the state of the deodorization apparatus.

What is claimed is:

1. A deodorization treatment apparatus comprising:

a deodorant tank configured to house microorganism-retaining carriers that retains microorganisms, the deodorant tank configured to be supplied with odorous gas, and the deodorant tank configured to discharge an exhaust gas in which an odor has been removed by the microorganisms;

a water sprinkler device configured to sprinkle treat water onto the microorganism-retaining carriers;

a water tank connected to the deodorant tank, the water tank configured to store treat water flowing out from the deodorant tank;

a water sprinkler pipe configured to supply treat water stored in the water tank to the water sprinkler device;

an exhaust pipe connected to a treatment facility that emits odorous gas and configured to supply the odorous gas to a lower part of the deodorant tank;

a first blower arranged in a path of the exhaust pipe for blowing the odorous gas;

a third blower configured to supply outside air to an upper part of the deodorant tank to dilute the exhaust gas;

an aeration device aerating the treat water stored in the water tank; and a control device configured to measure an ammonia concentration in the exhaust gas discharged from the deodorant tank, wherein the control device is configured to operate in a first control mode in which an inverter of the first blower is controlled to reduce the airflow rate; and wherein the control device is configured to operate in a second control mode in which an inverter of the third blower is controlled to increase the airflow rate, when a measurement result of the ammonia concentration in the exhaust gas exceeds a set value.

2. The deodorization treatment apparatus according to claim 1, further comprising:

a cooler arranged in the path of the exhaust pipe and configured to cool the odorous gas; and a gas flow resistance regulator arranged in the path of the exhaust pipe for adjusting the flow rate of the odorous gas, wherein the control device is configured to control a cooling capacity of the cooler or an opening degree of the gas flow resistance regulator.

3. The deodorization treatment apparatus according to claim 1, further comprising, a second blower configured to blow an outside air into the path of the exhaust pipe, wherein the control device is configured to control a blowing amount of the second blower.

4. The deodorization treatment apparatus according to claim 1, further comprising, a spraying device configured to spray a mist to the water tank, wherein the control device is configured to measure at least one of pH, temperature, an ammonia concentration, a NO concentration, a $NO_2$ concentration, a dissolved oxygen concentration, an electrical conductivity and a water level of the treat water in the water tank, and control at least one of the spraying of the mist to the water tank, a water supply to the water tank, or drainage from the water tank according to measurement result(s) of at least one of pH, temperature, the ammonia concentration, the NO concentration, the $NO_2$ concentration, the dissolved oxygen concentration, the electrical conductivity and the water level of the treat water in the water tank.

5. The deodorization treatment apparatus according to claim 1, wherein, the control device is configured to control at least one of watering amount or watering frequency of the water sprinkler device, amount of air bubbles generated in liquid of the aeration device, water supply to the water tank, drainage from the water tank, or temperature of the deodorant tank according to the measurement result of the ammonia concentration in the exhaust gas.

6. The deodorization treatment apparatus according to claim 1, further comprising, a demister arranged in the path of the exhaust pipe for filtering the odorous gas.

7. The deodorization treatment apparatus according to claim 1, wherein the control device is configured to manage states of the microorganisms by controlling an amount of drainage volume discharged from the water tank.

8. The deodorization treatment apparatus according to claim 1, further comprising:

a communication device connected to the control device and transmitting the measurement result of the ammonia concentration in the exhaust gas; and a client terminal located away from the control device, the client terminal configured to receive the measurement result of the ammonia concentration in the exhaust gas transmitted by the communication device, and the client terminal configured to display the measurement result of the ammonia concentration in the exhaust gas.

9. The deodorization treatment apparatus according to claim 8, wherein the client terminal is configured to transmit a control signal, the communication device is configured to receive the control signal, and the control device is configured to control at least one of blowing amount of the first blower, watering amount or watering frequency of the water sprinkler device, amount of air bubbles generated in liquid of the aeration device, water supply to the water tank, drainage from the water tank, or temperature of the deodorant tank according to the control signal received from the client terminal.

10. The deodorization treatment apparatus according to claim 8, further comprising, a sensor measuring the odor of the exhaust gas, wherein the control device is configured to control blowing amount of the first blower or amount of discharge of the exhaust gas according to the measurement result of the odor of the exhaust gas.

11. The deodorization treatment apparatus according to claim 1, wherein, the control device is configured to measure (1) a temperature of the odorous gas supplied to the deodorant tank, or (2) an internal pressure of the deodorant tank, and is configured to control the blowing amount of the first blower according to a measurement result of (1) the temperature of the odorous gas supplied to the deodorant tank, or (2) the internal pressure of the deodorant tank.

* * * * *